United States Patent
Doak et al.

(10) Patent No.: US 7,173,709 B2
(45) Date of Patent: Feb. 6, 2007

(54) MULTI-GRADE OBJECT SORTING SYSTEM AND METHOD

(75) Inventors: Arthur G. Doak, Nashville, TN (US); Mitchell Gregg Roe, Franklin, TN (US); Garry R. Kenny, College Grove, TN (US)

(73) Assignee: MSS, Inc., Nashville, TN (US)

( * ) Notice: Subject to any disclaimer, the term of this patent is extended or adjusted under 35 U.S.C. 154(b) by 0 days.

(21) Appl. No.: 11/325,835

(22) Filed: Jan. 5, 2006

(65) Prior Publication Data

US 2006/0109473 A1    May 25, 2006

Related U.S. Application Data

(62) Division of application No. 09/516,257, filed on Feb. 29, 2000, now Pat. No. 7,019,822.

(60) Provisional application No. 60/180,373, filed on Feb. 4, 2000.

(51) Int. Cl.
*G01N 21/47* (2006.01)

(52) U.S. Cl. .................................................. 356/446

(58) Field of Classification Search ................. None
See application file for complete search history.

(56) References Cited

U.S. PATENT DOCUMENTS

| | | | |
|---|---|---|---|
| 3,908,814 A | 9/1975 | Hieronymus | |
| 4,131,540 A | 12/1978 | Husome et al. | |
| 4,352,430 A | 10/1982 | Maier et al. | |
| 4,657,144 A | 4/1987 | Martin et al. | |
| 4,699,510 A | 10/1987 | Alguard | 356/73 |
| 4,741,042 A | 4/1988 | Throop et al. | 382/1 |
| 4,830,501 A | 5/1989 | Terashita | 356/402 |
| 4,919,534 A | 4/1990 | Reed | |
| 4,945,253 A * | 7/1990 | Frohardt | 250/559.16 |
| 5,085,325 A | 2/1992 | Jones et al. | |
| 5,139,339 A * | 8/1992 | Courtney et al. | 356/446 |
| 5,143,308 A | 9/1992 | Hally et al. | |
| 5,150,307 A | 9/1992 | McCourt et al. | |
| 5,165,676 A | 11/1992 | Blessing et al. | |
| 5,197,678 A | 3/1993 | Trezek et al. | |
| 5,297,667 A | 3/1994 | Hoffman et al. | |
| 5,315,384 A | 5/1994 | Heffington et al. | |
| 5,318,172 A | 6/1994 | Kenny et al. | |
| 5,333,739 A | 8/1994 | Stelte | |
| 5,335,791 A | 8/1994 | Eason | |
| 5,339,963 A | 8/1994 | Tao | |

(Continued)

FOREIGN PATENT DOCUMENTS

JP    11-084745    3/1999

OTHER PUBLICATIONS

DE 44 17 257 A 1.

(Continued)

*Primary Examiner*—Tu T. Nguyen
(74) *Attorney, Agent, or Firm*—Waddey & Patterson, P.C.; Lucian Wayne Beavers

(57) ABSTRACT

A paper sorting system allows the high speed determination of color, glossiness and the presence of printed matter for individual sheets of paper in a stream of waste paper. Sorting criteria may be selected from a plurality of predefined options to sort the paper stream.

15 Claims, 10 Drawing Sheets

U.S. PATENT DOCUMENTS

| | | | | |
|---|---|---|---|---|
| 5,398,818 | A | 3/1995 | McGarvey | |
| 5,402,264 | A | 3/1995 | Wilbur et al. | |
| 5,419,438 | A | 5/1995 | Squyres et al. | |
| 5,440,127 | A | 8/1995 | Squyres | |
| 5,443,164 | A | 8/1995 | Walsh et al. | |
| 5,464,981 | A | 11/1995 | Squyres et al. | |
| 5,469,973 | A | 11/1995 | Booth et al. | |
| 5,481,864 | A | 1/1996 | Wright | |
| 5,497,871 | A | 3/1996 | Ciolkevich | |
| 5,501,344 | A | 3/1996 | Kaiser et al. | |
| 5,512,758 | A | 4/1996 | Kobayashi et al. | 250/461.1 |
| 5,531,331 | A | 7/1996 | Barnett | |
| 5,533,628 | A | 7/1996 | Tao | |
| 5,555,984 | A | 9/1996 | Sommer, Jr. et al. | |
| 5,632,381 | A | 5/1997 | Thust et al. | |
| 5,675,416 | A | 10/1997 | Campbell et al. | |
| 5,689,757 | A * | 11/1997 | Ferrante et al. | 399/45 |
| 5,703,784 | A | 12/1997 | Pearson | 364/478.11 |
| 5,789,741 | A | 8/1998 | Kinter et al. | |
| 5,794,788 | A | 8/1998 | Massen | |
| 5,799,105 | A | 8/1998 | Tao | |
| 5,799,801 | A | 9/1998 | Clark et al. | |
| 5,813,542 | A | 9/1998 | Cohn | |
| 5,848,706 | A | 12/1998 | Harris | |
| 5,862,919 | A | 1/1999 | Eason | |
| 5,884,775 | A | 3/1999 | Campbell | 209/581 |
| 5,900,943 | A | 5/1999 | Owen | 356/445 |
| 5,901,856 | A | 5/1999 | Brantley, Jr. et al. | |
| 5,917,585 | A | 6/1999 | Roe et al. | |
| 5,954,206 | A | 9/1999 | Mallon et al. | |
| 5,960,964 | A | 10/1999 | Austin et al. | |
| 5,966,217 | A | 10/1999 | Roe et al. | |
| 5,979,240 | A | 11/1999 | Rix et al. | |
| 6,064,056 | A | 5/2000 | Doak | |
| 6,076,684 | A | 6/2000 | Bollegraaf | |
| 6,137,074 | A | 10/2000 | Doak | |
| 6,263,291 | B1 | 7/2001 | Shakespeare et al. | 702/85 |
| 6,335,501 | B1 | 1/2002 | Khalfan | 209/582 |
| 6,369,882 | B1 | 4/2002 | Bruner et al. | 356/73 |
| 6,373,575 | B1 | 4/2002 | Takayama et al. | 356/445 |

OTHER PUBLICATIONS

PCT/DE95/00966.

* cited by examiner

MULTI-GRADE OBJECT SORTING SYSTEM AND METHOD

This application is a divisional of U.S. patent application Ser. No. 09/516,257 filed Feb. 29, 2000, now U.S. Pat. No. 7,019,822 issued Mar. 28, 2006, which parent application claimed benefit of provisional U.S. patent application Ser. No. 60/180,373, filed Feb. 4, 2000, and which parent application also was a continuation-in-part of co-pending U.S. patent application Ser. No. 09/301,715, filed Apr. 29, 1999, entitled "SYSTEM AND METHOD FOR SENSING WHITE PAPER", by Bruner et al., now U.S. Pat. No. 6,369,882 issued Apr. 9, 2002. The present application claims benefit of each of the noted prior applications.

BACKGROUND OF THE INVENTION

1. Field of the Invention

The present invention relates generally to a multi-grade object sorting system and method and more particularly to such a system for sorting various grades and colors of paper.

2. Description of the Prior Art

The high speed sorting of waste paper has only recently become feasible with the introduction of a system by the Assignee of the present invention as described in pending U.S. patent application Ser. No. 09/301,715, filed Apr. 29, 1999, entitled "System and Method for Sensing White Paper", by Bruner et al., the details of which are incorporated herein by reference. The first such system as described in the aforementioned application, could only identify and separate white office paper. The technique utilized for identifying and distinguishing such paper was the presence of the fluorescence of the paper when subjected to ultraviolet light.

It has been proposed to sort paper based on color as described in European Patent Publication No. EP0873797A2, published on Oct. 28, 1998. The European patent publication proposed to utilize visible light, ultraviolet light, x-rays and/or infrared light to illuminate the paper, while observing the reflected light with one or more cameras connected to a central processing unit. The disclosure of the European patent office publication is very vague with regard to the manner in which such a process could be conducted, and its sorting system utilizes mechanical pickers thus indicating that the system would operate at relatively low speeds.

Sorting systems for other objects other than paper are available which utilize red, green and blue light emitting diodes as light sources. An example is a product sold by the Assignee of the present invention is described in pending U.S. patent application Ser. No. 09/183,349 filed Oct. 30, 1998 by Doak, the details of which are incorporated herein by reference.

Thus, it is seen that there is a need for a system capable of sorting paper based upon the color of the paper, and capable of doing so at sufficiently high speeds as to make the process economical. Such a system, along with various refinements thereof is the subject of the present invention.

SUMMARY OF THE INVENTION

A method is providing for sorting paper. The paper is conveyed through an inspection zone. As the paper passes through the inspection zone at least three characteristics of the paper are analyzed, including the color of the paper, whether the paper is glossy, and whether the paper displays printed material. The paper is then sorted based upon at least one of the analyzed characteristics.

In another embodiment of the invention, an apparatus is provided for sorting paper. The apparatus includes a conveyor for conveying paper through the inspection zone. A light source is provided for transmitting light onto the paper in the inspection zone. A sensor is provided for receiving light reflected from the paper in the inspection zone. The apparatus includes a paper analysis system, operably connected to the sensor for receiving the reflected light signals therefrom. The paper analysis system includes a color determination component, a glossiness determination component, and a printed matter determination component. A sorting mechanism is included to sort the paper between a select path and a reject path. The sorting mechanism is operably connected to the paper analysis system for sorting paper in response to the analysis conducted by the paper analysis system.

In another embodiment of the invention a high speed method is provided for sorting paper. The paper is conveyed through an inspection zone at a speed of at least 1,000 feet per minute, and preferably at least 1,500 feet per minute. As the paper passes through the inspection zone at least one characteristic thereof is analyzed, the at least one characteristic being selected from the group consisting of color, glossiness and the presence of printed matter. The paper is sorted downstream of the inspection zone based upon the analysis of the at least one characteristic.

In yet another embodiment of the invention, a method is provided for sorting paper based upon the color of the paper. First, the paper is moved through an inspection zone. The paper in the inspection zone is exposed to a plurality of separate beams of visible light of different wavelengths. A color of the paper is analyzed based upon a comparison of the paper reflectivity of the different wavelengths of visible light. Then the paper is sorted downstream of the inspection zone based upon the color of the paper.

In still another embodiment of the invention, a method is provided for analyzing the color of a moving object. The object is moved within an inspection zone. The inspection zone is sequentially interrogated with multiple light sources of different light wavelengths as the object moves within the inspection zone. The interrogation includes a first series of sequential flashes of the multiple light sources in a first order, followed by a second series of sequential light flashes of the multiple light sources in a second order which is the inverse of the first order. Then the reflections of the multiple light sources from the paper are analyzed. The analysis includes consideration of two reflections originating from each light source, one of the reflections occurring during the first series and the other of the two reflections occurring during the second series. Preferably, the two reflections are averaged to approximate the color which would be sensed if the paper was not moving at the time of interrogation.

In another embodiment of the invention, a paper sorting apparatus is provided which includes a conveyor for conveying paper through an inspection zone, the conveyor having a width. A light transmitter transmits light onto the paper in the inspection zone. The light transmitter includes an array of red lights, an array of green lights, and an array of blue lights, each array being spaced across the width of the conveyor. A light receiver receives light reflected from paper in the inspection zone. The light receiver includes an array of sensors spaced across the width of the conveyor. Each sensor receives light reflected from an area defining one pixel of the paper.

In another embodiment of the invention, a method is provided for sorting paper. The paper is moved through an inspection zone. Light is transmitted onto the paper in the inspection zone. Light reflected from the paper is collected. Then parameters of the light collected from adjacent portions of the paper within the inspection zone are compared to identify paper with a varying reflectance from adjacent portions resulting from a presence of printed matter on the paper. The paper is then sorted based upon the presence of printed matter.

In another embodiment of the invention, a paper sorting method is provided. The paper is moved through an inspection zone. A first light beam is transmitted from a first source onto the paper. The method then includes receiving a diffused reflected first light beam which is reflected from the paper as a result of the first light beam. A second light beam is transmitted from a second source onto the paper. The method includes receiving a directly reflected second light beam reflected from the paper as a result of the second light beam. The glossiness of the paper is analyzed based upon a comparison of the diffuse reflected first light beam to the directly reflected second light beam. The paper is sorted based upon the glossiness of the paper.

In another embodiment of the invention, an apparatus is provided for sorting paper based upon glossiness. The apparatus includes a conveyor for conveying paper through an inspection zone. First and second light sources are provided for transmitting light onto the inspection zone. A sensor receives light reflected from the inspection zone. The first light source is oriented so that the sensor receives diffuse reflected light from the first light source. The second light source is oriented so that the sensor receives directly reflected light from the second light source.

Another embodiment of the invention provides a method for sorting paper which utilizes an array of sensors and provides a technique for normalizing the array of sensors. The method includes conveying the paper through an inspection zone. Light is transmitted from an array of light sources onto a mirror. The mirror reflects the light onto the inspection zone, where it reflects off the paper in the inspection zone back to the mirror. That reflected light which is once again reflected off the mirror is received in an array of sensors which sensors generate signals corresponding to characteristics of the paper in the inspection zone. The mirror can be moved to a normalization position wherein light from the array of light sources is reflected from the mirror onto a reference surface. Outputs from the array of sensors can be normalized with reference to the light reflected off of the reference surface.

It is therefore an object of the present invention to provide improved paper sorting methods and apparatus.

Another object of the present invention is to provide methods and apparatus for sorting paper based upon color of the paper.

Still another object of the present invention is the provision of methods and apparatus for sorting paper based upon the glossiness of the paper.

And another object of the present invention is the provision of methods and apparatus for sorting paper based upon the presence of printed matter on the paper.

Still another object of the present invention is the provision of apparatus and methods whereby paper can be sorted based upon any desired combination of color, glossiness and the presence of printed matter.

Still another object of the present invention is the provision of a paper sorting method and apparatus utilizing an array of sensors, and providing a technique for normalization of the array of sensors.

Other and further objects, features and advantages of the present invention will be readily apparent to those skilled in the art upon a reading of the following disclosure when taken in conjunction with the accompanying drawings.

DETAILED DESCRIPTION OF THE PREFERRED EMBODIMENTS

Figure 1:
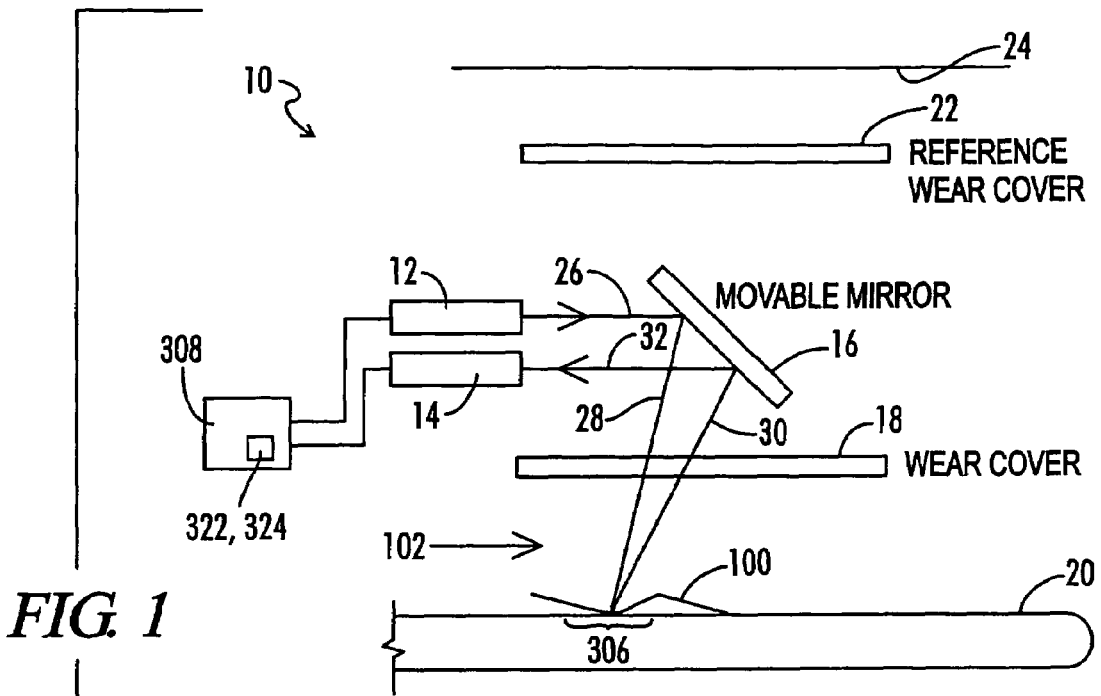
FIG. 1 is a side view of the system and method of the preferred embodiment in an operating position.

Referring now to FIG. 1 there is shown generally at 10, the multi-grade object sorting system and method of the present invention. FIG. 1 shows the preferred embodiment in which transmitter or first light array 12 transmits light along transmitted light pathway 26 into mirror 16 which then redirects the transmitted light along redirected transmitted light path 28 onto object 100 which is preferably paper. The light reflected from object 100 travels along reflected light path 30 onto mirror 16 which then redirects the reflected light along redirected reflected light path 32 into receiver 14. In each case, the light passes through wear cover 18 which protects the mirror 16 from object path 102 while object 100 is traveling along belt 20. Although FIG. 1 shows the preferred embodiment, it should be understood that movable mirror 16, although adding features unique to the preferred embodiment, can be removed with transmitter 12 directing light directly onto object 100 which would make the transmitter light path direct instead of bifurcated into transmitted light path 26 and redirected transmitted light path 28. Likewise, the receiver can receive the reflected light directly from object 100 instead the reflected light of being divided into reflected light path 30 and redirected reflected light path 32.

Figure 8:
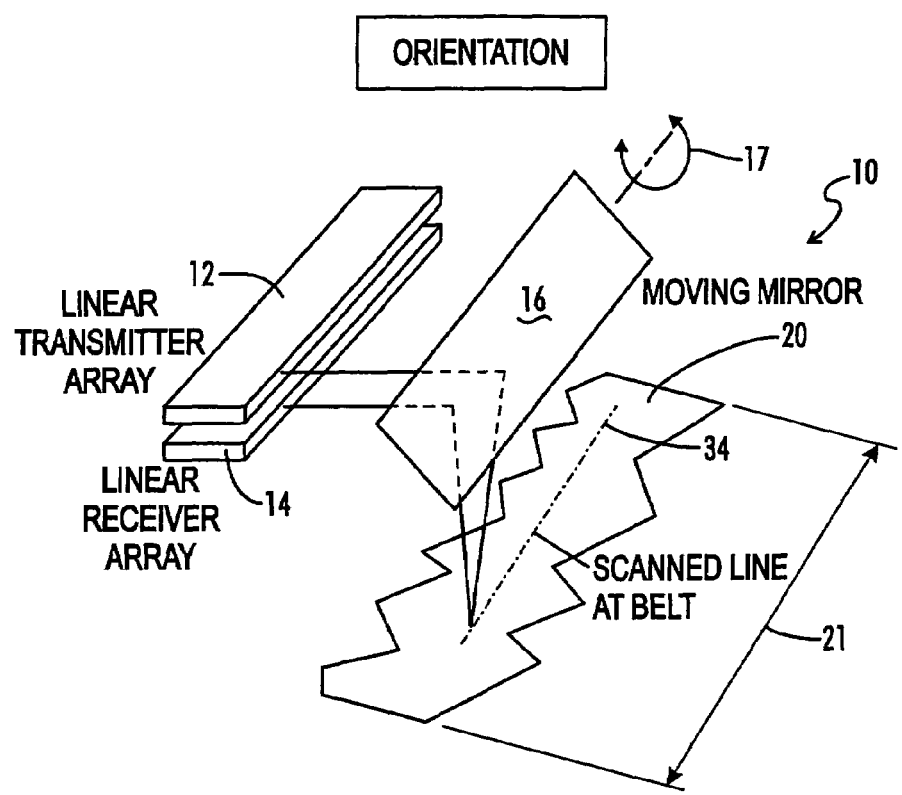
FIG. 8 is a perspective view of the sorting system.

The conveyor belt 20 has a width 21 as seen in FIG. 8. Conveyor belt 20 is typically a black rubberized belt.

Figure 2:
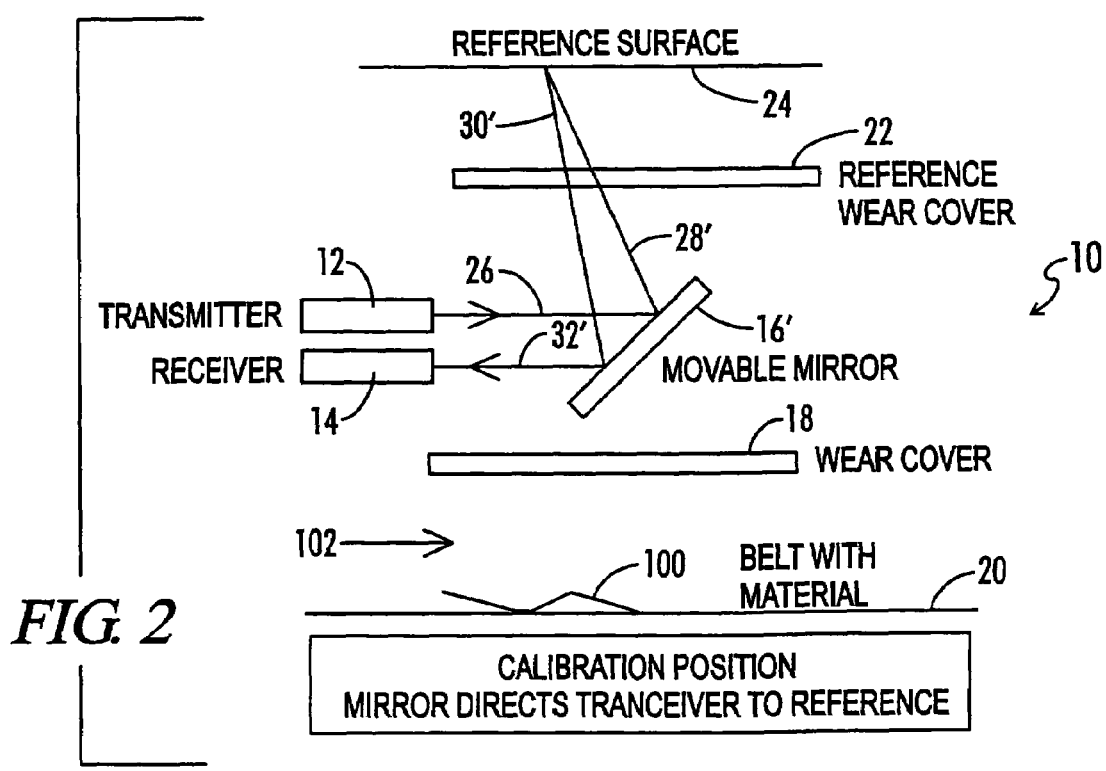
FIG. 2 is a side view of the method and system in a calibration position.

Referring now to FIG. 2 there is shown generally at 10, the multi-grade object sorting system and method of the present invention shown in calibrating or normalization position. In this instance, transmitter 12 transmits light along the same transmitted light path 26 shown in FIG. 1. However, mirror 16 is now in calibration or normalization position 16' which, in turn, reflects redirected transmitted light 26 along redirected transmitted light path 28' into and through reference wear cover 22 onto reference surface 24. In the preferred embodiment, reference surface 24 is a constant color which is, preferably, white Teflon. The white Teflon surface maintains a constant color over time, which should, over time, reflect a consistent color along reflected light path 30' against mirror 16' which redirects reflected light 30' along redirected reflected light path 32' into receiver 14. In calibration or normalization position, an analyzing computer system or systems will realize what the readings from the receiver 14 should be when light from transmitter 12 is reflected against reference surface 24 and will factor in the normalization to make sure that all sensors are read uniformly so as to not effect the sorting ability of system and method 10. Above mirror 16 is placed reference wear cover 22 which, in turn, is intended to make light from reference surface 24 have the same optical properties as light passing through wear cover 18 over conveyor belt 20. In other words, wear cover 18 actually affects the amount of light passing through it. Therefore, to ensure proper normalization, reference wear cover 22 is interposed along redirected transmitted light path 28' and reflected light path 30'.

Figure 3:
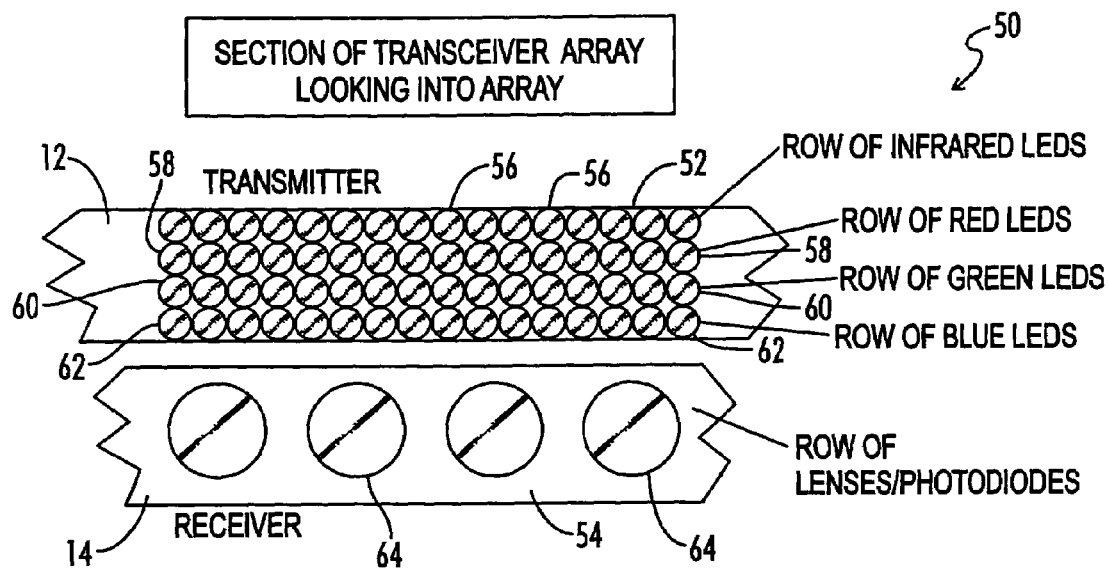
FIG. 3 is a frontal view of the transmitter and receiver array of the preferred embodiment.

Referring now to FIG. 3 there is shown generally at 50, part of the preferred transmitter and sensor arrays of the present invention that makes up transmitter 12 and receiver 14, respectively. Transmitter 12 includes transmitter array 52 which includes various rows of light emitting diodes (LEDs). Likewise, receiver array 54 of receiver 14 contains a row of lenses and photo diodes.

In the preferred embodiment, transmitting array 52 consists of a row of infrared LED's 56, a row of red LED's 58, a row of green LED's 60 and a row of blue LED's 62. Until very recently, there was no source of adequate blue LED's 62. In the preferred embodiment, infrared LED's 56 are of the type such as HSDL-4230 manufactured by Hewlett Packard. Red LED's 58 are of the type such as KR5004X manufactured by Stanley. Green LED's 60 are of the type such as HLMP-CM15 manufactured by Hewlett Packard. Blue LED's 62 are of the type such as HLMP-CB15 manufactured by Hewlett Packard. In the preferred embodiment, receiver array 54 contains multiple lens and photo diode pairs 64.

Figure 4:
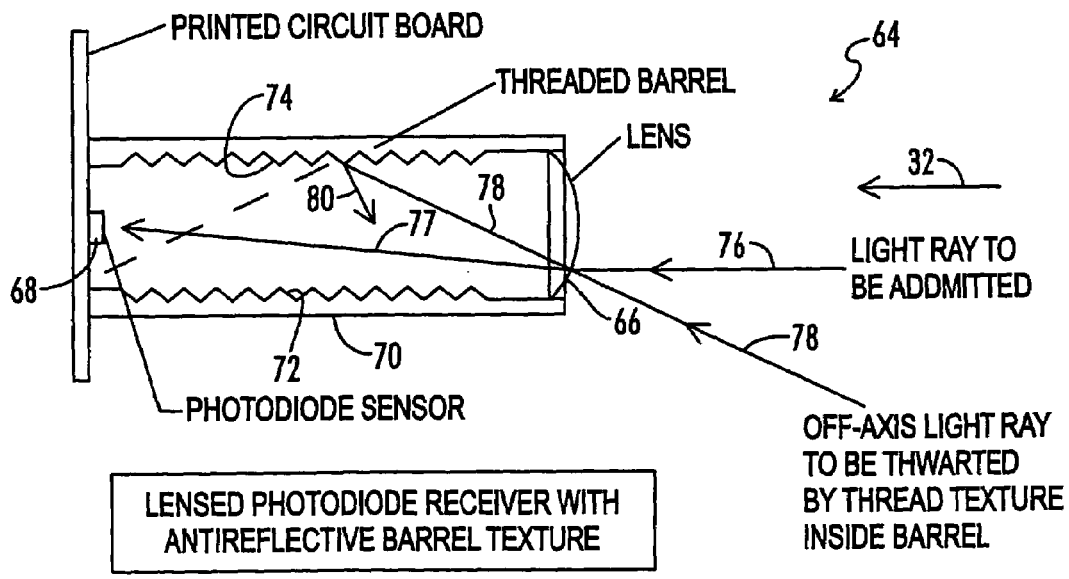
FIG. 4 is a cutaway view showing the photo diode receiver with anti-reflective barrel texture of the present invention.

Referring now to FIG. 4, there is shown generally at 64 a cutaway view of one lens/photo diode pair of the present invention. As can be seen in FIG. 4, lens 66 receives light from mirror 16 (not shown) and directs it onto photo diode sensor 68. In the preferred embodiment, lens photo diode pair housing 70 has interior surface 72 having threads 74. Threads 74 perform the function of preventing unwanted redirected reflective light 32 from being received by photo diode 68. As can be seen, admissible light which is generally parallel to the axis of housing 70, travels along admissible light path 76 through lens 66 which focuses the light along focal path 77 onto photo diode 68. Conversely, inadmissible light, which is classified as light which is off the axis of the light array, which probably means that the light is coming from a position on the object 100 that does not need to be analyzed, passes along inadmissible light path 78, bounces off thread 74 and bounces along bounce path 80 for inadmissible light which misses photo diode 68.

Each photo diode 68 and lens 66 is constructed so that the photo diode 68 is sensitive to incident light having a deviation from axial of less than about 3°. This may be referred to as a receiver or telescope. Each receiver will receive light from a target area on a surface about two feet away which is about ¾" to 1" in diameter. The receivers are arrayed at a 0.75" spacing linearly to form a linear array.

Figure 5:
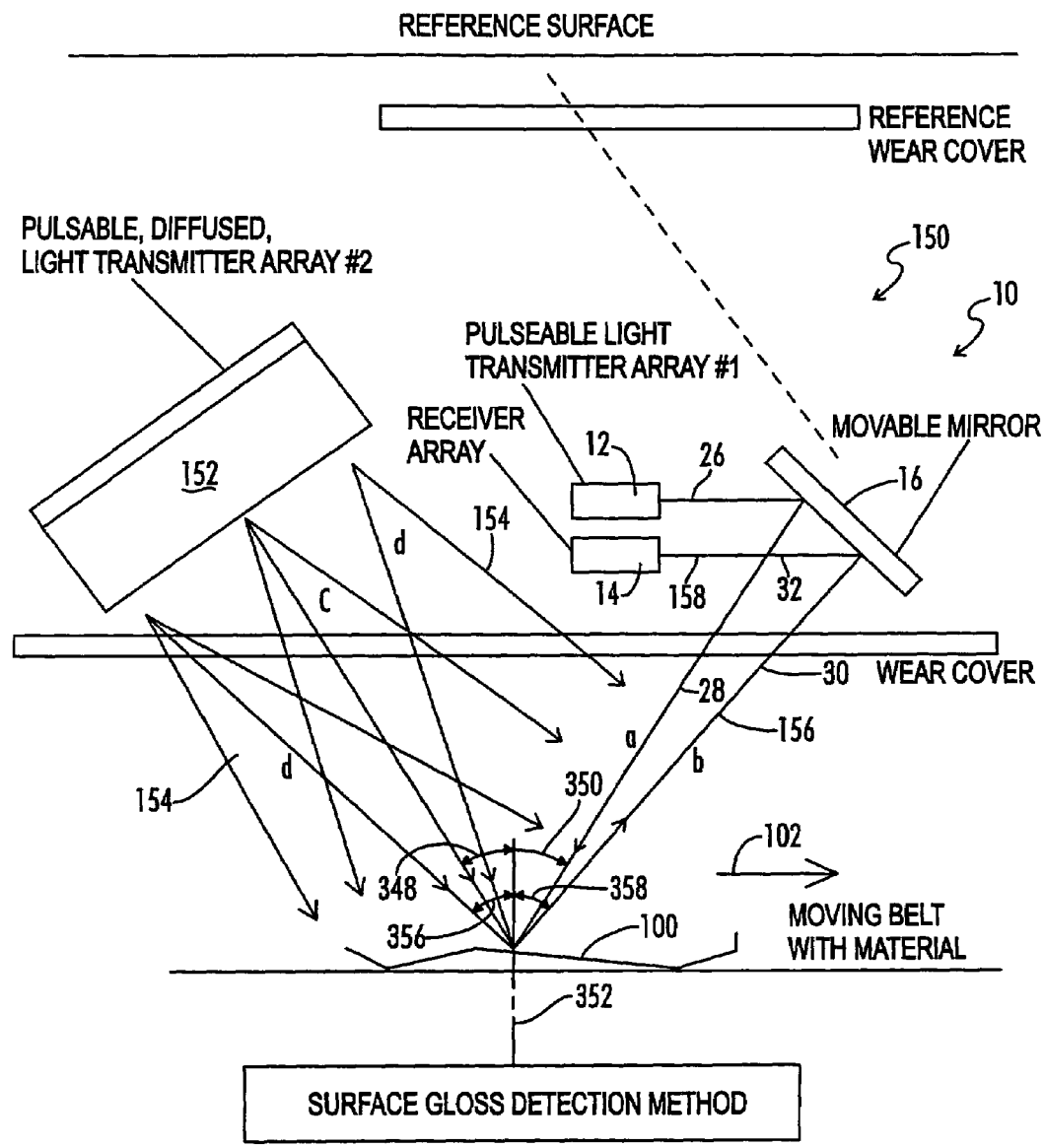
FIG. 5 is a side view of the surface gloss detection method of the present invention.

Referring now to FIG. 5, there is shown another aspect of the multi-grade object sorting system and method of the present invention. In this particular drawing, the surface gloss detection system and method 150 is shown. The sensor and receiver layout shown in FIG. 1 senses paper by grade and by color and is directed at a given angle. The degree of surface gloss of paper or other objects 100 needs to be determined in order to make a more accurate sort. Accordingly, surface gloss detection system and method 150 uses light transmitter array 152 that can be pulsable and diffused in the preferred embodiment. Light from transmitter array 152 passes along diffused path 154 onto object 100. In the preferred embodiment, light transmitter array 152 is pulsable so that light transmitter array 152 can be turned on and off very quickly thereby alternating with the different colored LED's shown in FIG. 3. Therefore, diffused light passes along diffused light path 154 onto object 100. If the paper 100 is glossy, a substantial portion of the light energy will be directly reflected along pathway 156 onto mirror 16 and then along pathway 158 into receiver 14. If the reading from light transmitter or array number 152 is greater than light transmitter array number 12, then there is gloss. If the two readings are equal, then there is no gloss. In the preferred embodiment, the light from transmitter 12 and transmitter array 152 is infrared when measuring for gloss.

The first and second light beams from sources 12 and 152 are transmitted at approximately equal but opposite angles 348 and 350 on opposite sides of an imaginary plane 352 normal to the direction 102 in which the paper 100 is moving. The second source 152 is physically wide and made up of a number of individual sources thus providing what may be generally described as a wide and diffuse source so that the light 154 therefrom is directed at a variety of angles generally directed toward the paper 100. This allows paper 100 that is somewhat crumpled or not lying exactly parallel upon the belt 20 to be examined for glossiness, because at least some of the rays from wide and diffuse source 152 will strike the surface of the paper 100 in such a manner as to directly reflect along path 156 to the mirror 16 and then to the receiver 14. Infrared light is preferred for use in the gloss detection because most inks utilized on printed matter will reflect a lot of infrared light, even black inks, whereas if a colored light were used for the gloss detection, some inks would absorb much of that color. Also, infrared light emitting diodes are cheaper than visible light colored light emitting diodes, and thus all else being equal the infrared LED is preferred. It will be understood, however, that glossiness detection could be achieved in a somewhat less efficient manner by use of a colored light source.

Figure 6:
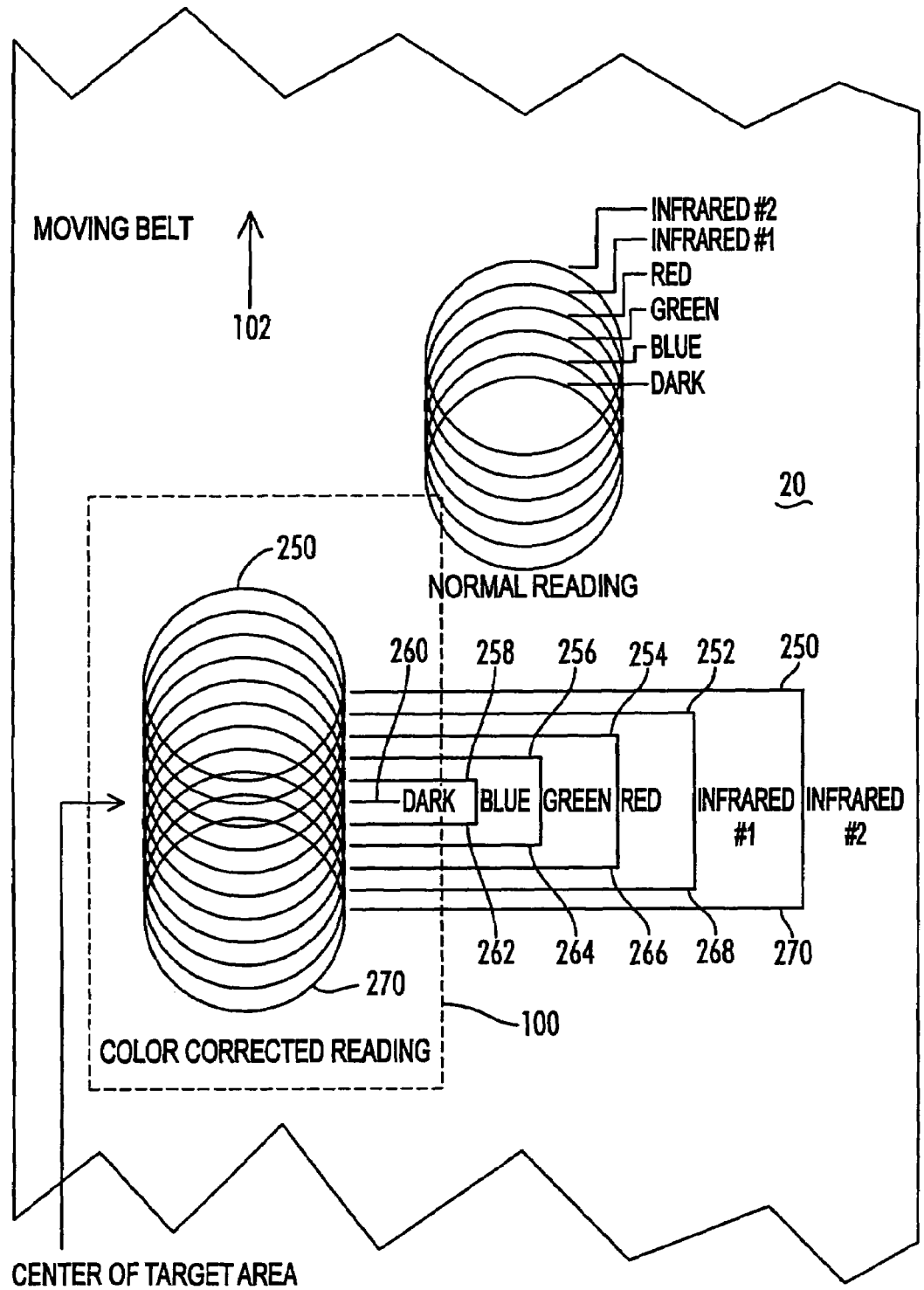
FIG. 6 is a drawing showing the LED normal versus corrected readings of the system and method of the present invention.

Referring now to FIG. 6, there is shown the colored corrected readings of the preferred embodiment. Each circle on belt 20 represents a circular reading of light reflected from belt 20. As object 100 passes along path 102, the infrared LEDs from second light array 152 are flashed onto second infrared first spot 250 and read by receiver 14. Then the infrared LEDs from first light array 12 are flashed onto first infrared first spot 252 and read by receiver 14. Then the red LEDs from first light array 12 are flashed onto red first spot 254 and read by receiver 14. Then the green LEDs from first light array 12 are flashed onto green first spot 256 and read by receiver 14. Then the blue LEDs from first light array 12 are flashed onto blue first spot 258 and read by receiver 14. Then the no light is flashed onto dark spot 260 and read by receiver 14. Then the blue LEDs from first light array 12 are flashed onto blue second spot 262 and read by receiver 14. Then the green LEDs from first light array 12 are flashed onto green second spot 264 and read by receiver 14. Then the red LEDs from first light array 12 are flashed onto red second spot 266 and read by receiver 14. Then the first infrared LEDs from first light array 12 are flashed onto first infrared second spot 268 and read by receiver 14. Finally, the infrared LEDs from second light array 152 are flashed onto second infrared second spot 270 and read by receiver 14. In summary, initially, infrared number 2 will flash, then infrared number 1 will flash followed by, in preferred order, red, green, blue, dark, blue, green, red, infrared number 1 and infrared number 2. The purpose behind bracketing the colors on each side of center is that with the passage of time and the objects along a moving belt, the very center of the target area cannot be flashed with every color at a single given time. Therefore, the center value is approximated by averaging the like color values. Although FIG. 6 shows the preferred order of flashing, any other sequence of flashing could also work as well.

Figure 7:
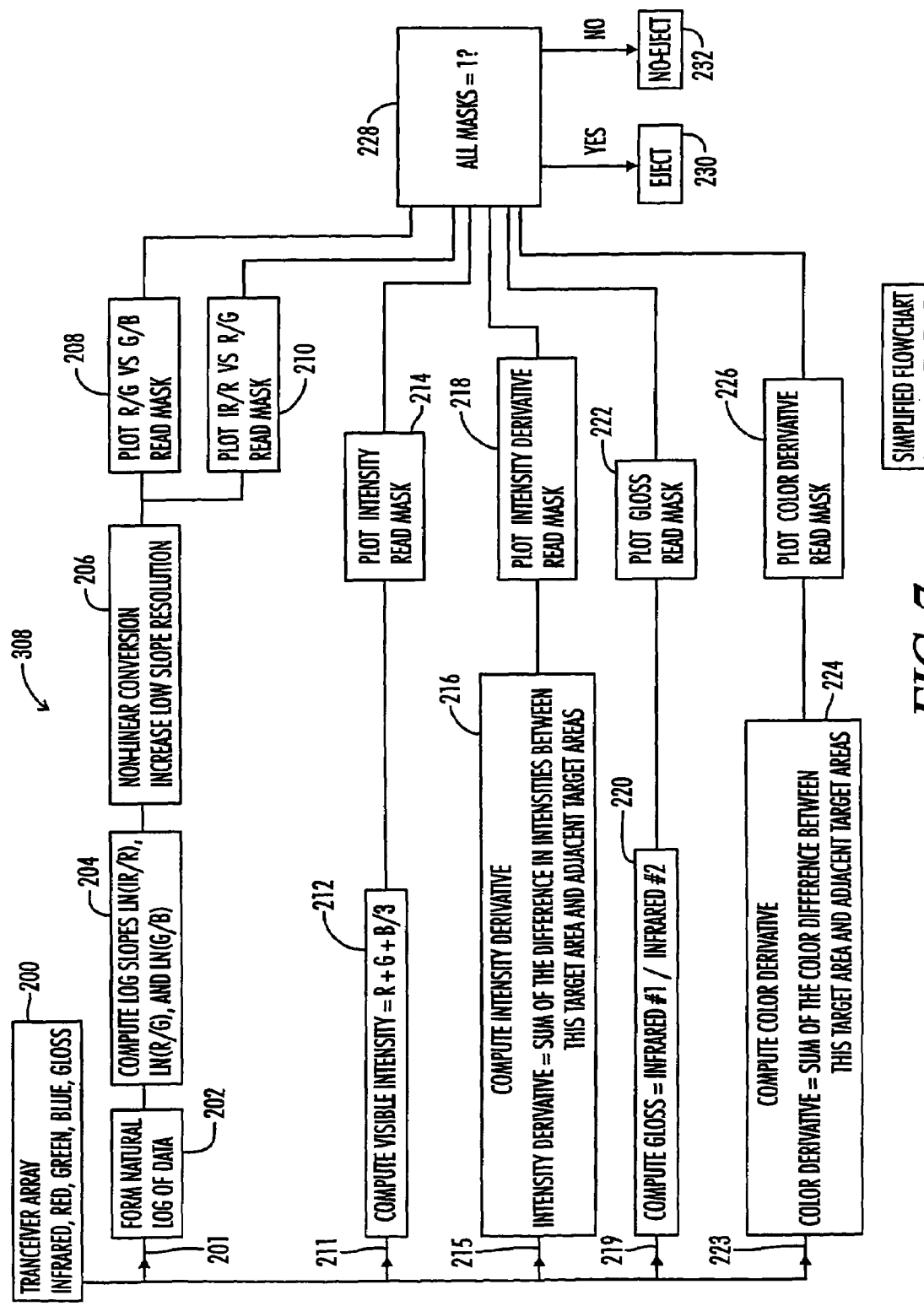
FIG. 7 is a flow chart which illustrates the manner in which the received signals from the various light sources are analyzed to determine the category of paper passing through the inspection zone.

Referring now to FIG. 7, there is shown a simplified flow chart of how the system analyzes the data received by receiver 14 as shown in FIGS. 1 and 5.

Initial step 200 is reading the transceiver array of the infrared, red, green, blue, and gloss sensors and averaging the two sensor readings received from each light source.

This information is then further analyzed in five concurrent processes 201, 211, 215, 219 and 223 beginning with steps 202, 212, 216, 220, and 224, respectively.

Initial or color comparison process 201 essentially compares the logs of the intensities of the reflected light received from each of the light sources. Initial or color comparison process 201 begins with the step 202 of forming the natural logs of the data obtained during step 200. After the natural logs 202 have been formed or determined, the log slopes of the infrared readings divided by the red readings (ln(IR/IR)), the red readings divided by the green readings (ln(R/G)), and the green readings divided by the blue readings (ln(G/B)) are computed in step 204. The advantage of using logarithm ratios is that it avoids taking a division step which is very time consuming for the microprocessor.

Step 204 is followed by a step 206 of performing a non-linear conversion for each log slope that increases the low slope resolution. This non-linear conversion 206 is followed by concurrent steps 208 and 210. Step 208 is plotting the LN (R/G) v. LN (G/B) on a two dimensional map and reading the mask out from the map. Step 210 which is plotting the log infrared/red versus the log red/green on a separate two-dimensional map and reading the mask out. A mask is a binary data comprising either a one or a zero.

Second concurrent or visible intensity computing process 211 begins with step 212 which is computing the intensity (red plus green plus blue data from step 200). Following step 212 is step 214 of plotting of the intensity (red plus green plus blue divided by 3) on a one-dimensional map and the reading of a mask.

Third concurrent or intensity derivative process 215 after step 200 is step 216 of computing intensity derivative. The intensity derivative is defined as the sum of the difference in the intensities between the target area and the adjacent target areas. The intensity derivative will provide a measure of the amount that the intensity varies from point to point on the object. For example, a piece of white paper has an intensity derivative of zero whereas a sheet of paper with printing will have a higher intensity derivative because the intensity changes from point to point based upon the various spaces with or without ink. After step 216, the intensity derivative is plotted on a one-dimensional map and a mask is read in step 218.

Fourth concurrent or gloss computing process 219 following step 200 begins with step 220 which is computing the gloss using the direct reflected infrared light from transmitter 152 divided by the diffuse reflected infrared light from transmitter 12. Following step 220 the gloss is plotted on a one dimensional map and the mask is read in step 222.

Fifth concurrent or color derivative process 223 after step 200 is computing the color derivative 224. The color derivative will provide a measure of the amount that the color varies from point to point on the object. For example, a piece of white paper has an color derivative of zero whereas a sheet of paper from a color magazine will have a higher color derivative because the color changes from point to point based upon the varying amounts color. Following step 224, the color derivative is plotted on a one-dimensional map and a mask is read from the map in step 226.

In the preferred embodiment, processes 201, 211, 215, 219 and 223 are concurrent to save time. However, they can be sequential or some of them can be concurrent.

The masks from steps 208, 210, 214, 218, 222, and 226 are then combined in step 228 using a Boolean function in such a way that if all readings from steps 208, 210, 214, 218, 222, and 226 are 1's, then ejection step 230 occurs. Otherwise no ejection occurs in non-ejection step 232.

The maps are analyzed based upon predetermined ranges based upon the sort desired. The criteria and ranges used to determine whether a 1 or 0 is assigned depends upon the desired results depending upon the type and color of papers sought to be sorted out.

Some readings for the various calculations are as follows. Example values for several types of paper are shown in the following Table I:

TABLE I

|  | White (printed) | b + w newspaper | magazine | brown cardboard |
| --- | --- | --- | --- | --- |
| ln(ired/red) | 0 | +.2 | −2 to +2 | +1 |
| ln(red/grn) | 0 | +.2 | −2 to +2 | +1 |
| ln(grn/blu) | 0 | +.2 | −2 to +2 | +1 |
| color derivative | 0–10% | 0–10% | 50–100% | 0–10% |
| Intensity | 70–100% | 30–70% | 20–100% | 30–60% |
| Intensity derivative | 0–50% | 0–50% | 0–60% | 0–10% |
| gloss | 0–30% | 0–30% | 30–80% | 0–20% |

These values show that each category of paper may be identified uniquely. Where there is overlap in the color identification, one of the other quantities may be used the resolve the final category identification. For example, a white area on a magazine would not be confused with white paper because the gloss and color derivative values are different.

It is also noted that the white paper being sorted typically includes black print material, so that there will be a measurable intensity deviation for "white" paper.

It will be understood that the color determination can be accomplished more precisely by examining characteristics in addition to the individual intensities of reflection of the various color components such as red, green and blue. For example, the overall reflectance or intensity of reflectance of all colors can help distinguish between a dark blue and a light blue.

FIG. 8 is a perspective view of the multi-grade object sorting system and method of the present invention. As can be seen, transmitter 12 is actually an array with receiver 14 also being an array. Mirror 16 is shown in operative position, but can be pivoted about mirror axis 17. As can be seen, in the preferred embodiment, at any one flash in time, a series of adjacent areas along scan line 34 are illuminated.

SUMMARY OF THE APPARATUS

Figure 9:
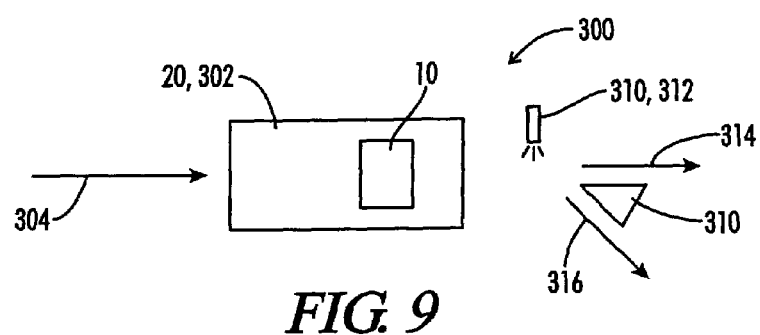
FIG. 9 is a schematic illustration of a paper sorting apparatus including the sorting system of FIG. 1.

Referring now to FIG. 9, a schematic illustration is there shown of a system 300 for sorting paper. The system 300 includes a mechanical conveyor system 302 which is preferably constructed generally in accordance with pending U.S. patent application Ser. No. 09/301,715, entitled "System and Method for Sensing White Paper", of Bruner et al. filed Apr. 29, 1999 which is assigned to the Assignee of the present invention and the details of which are incorporated herein by reference. The conveyor belt 20 is a part of the mechanical conveyor 302. The mechanical conveyor 302 takes an incoming stream 304 of waste paper and spreads it into a high speed moving stream of individual papers, a single layer thick, which are moving at speeds in excess of 1,000 feet per minute, and preferably speeds of at least 1,500 feet per minute.

The sorting system 10 described above with reference to FIGS. 2 and 3 is a part of the mechanical conveyor system 302. As seen in FIG. 1, a portion of the belt 20 which is observed by the receiver 14 may be generally described as an inspection zone 306. The conveyor 20 conveys the paper 100 through the inspection zone 306.

The transmitter 12 of FIG. 1 may be generally described as a light source 12 for transmitting light onto paper 100 in the inspection zone 306. The receiver 14 of FIG. 1 may be generally described as a sensor 14 for receiving light reflected from the paper 100 in the inspection zone 306.

A control system 308 is connected to the light source 12 and the sensor 14 is shown in FIG. 1, for controlling operation of the light source 12 as previously described, and for receiving data from the sensor 14. The microprocessor of control system 308 is programmed in accordance with the functions described above with regard to FIG. 7 in order to perform the analysis. The control system 308 may also be described as a paper analysis system 308 operably connected to the sensor 14 for receiving reflected light signals therefrom. The paper analysis system 308 includes a color determination component which includes processes 201 and 211. System 308 further includes a glossiness determination component which includes process 219. The system 308 further includes a printed matter determination component which includes processes 215 and 223.

Based upon the analysis of FIG. 7, the control system 308 also activates a sorting mechanism 310 which is schematically illustrated in FIG. 9. The sorting mechanism uses means such as, for example, air jets 312 for sorting the paper 100 into a select path 314 and a reject path 316. Again, the details of construction of the sorting mechanism 310 are shown in pending U.S. patent application Ser. No. 09/301, 715, entitled "System and Method for Sensing White Paper", of Bruner, et al., filed on Apr. 29, 1999, and assigned to the Assignee of the present invention, the details of which are incorporated herein by reference. The sorting mechanism 310 sorts the paper between the select path 314 and the reject path 316 in response to signals from the control system 308 and in accordance with the analysis conducted by the process illustrated in FIG. 7.

The control system or paper analysis system 308 has stored therein data, such as that provided above in Table I, which data corresponds to pre-determined values of parameters corresponding to color, glossiness and presence of printed matter for a plurality of categories of paper such as those described in Table I.

The color determination component processes 201 and 211, the glossiness determination component process 219, and the printed matter determination component processes 215 and 223 each are constructed to determine parameters for paper 100 of unknown category passing through the inspection zone 306 and to compare the parameters of the paper of unknown category to the stored data such as that of Table I.

Although the sorting system 10 is highly flexible and is capable of analyzing many different variables and identifying many different categories of paper, it will be understood that typically the system 10 will be set up to separate a given stream of paper into two resulting streams, namely the select path 314 and the reject path 316. It will be understood that the reject path 316 may in fact be made up of very valuable material, and that typically the reject stream 316 will simply be the divided fraction which is the smallest. For example, if the incoming stream 304 were primarily white office paper with a relatively small proportion of colored paper, cardboard or other miscellaneous items contained therein, the reject stream would be selected to be anything which is not white office paper.

Figure 10:
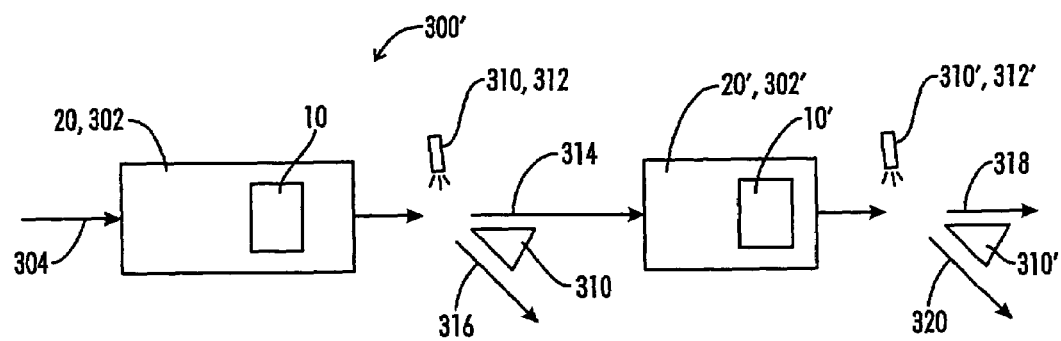
FIG. 10 is a schematic illustration similar to FIG. 9 showing two paper sorting systems in series.

If it is desired to separate an incoming stream into more than two fractions, then typically two sorting systems 10 and 10' would be placed in series as shown in FIG. 10. The select path 314 from the first system would become the incoming stream to a second sorting system 10' and would then be sorted into a second select path 318 and a second reject path 320.

The control system 308 includes a human interface system 322 which includes a sort selection touch screen input panel 324. The human interface system 322 includes a plurality of predefined options for sorting of predefined categories of paper so that a human operator of the sorting system 10 may select one of the predefined options to be implemented by the paper analysis system 308 and the sorting mechanism 310.

Figure 11:
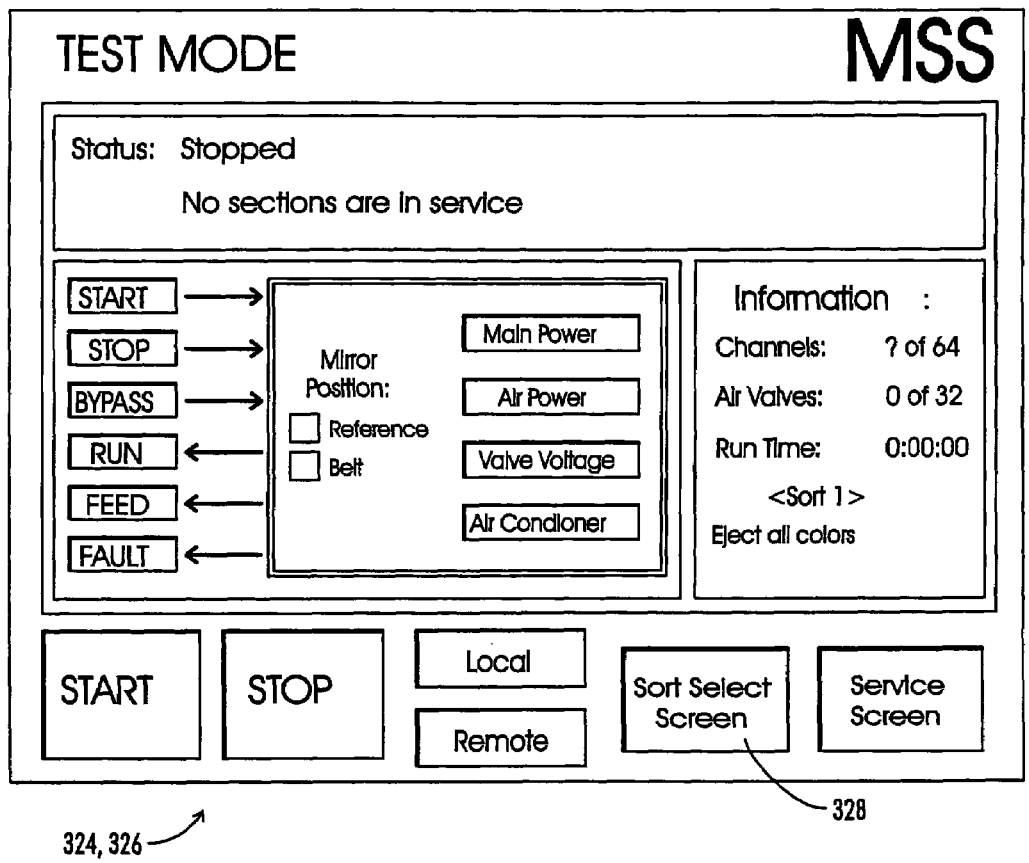
FIG. 11 illustrates a home screen of a human interface touch screen system.

FIG. 11 illustrates a first screen display of the sort selection touch screen input panel 324, which is generally designated by the numeral 326. The first screen or home screen 326 displays indicia corresponding to whether the paper sorting apparatus 300 is running, whether there are any current faults indicated, such as low air pressure or the like, and what the current paper sort selection criteria is. By touching a sort select button 328, the user is taken to a sort select screen 330 illustrated in FIG. 12. The sort select screen 330 illustrated displays sixteen individual options, each of which is associated with a predefined paper selection option. Each option will display text descriptive thereof. For example, option 332 is associated with the predefined option to "PASS WHITE PAPER; EJECT ALL COLORED PAPER". Similarly, the selection 334 is associated with the predefined option of "EJECT ALL WHITE PAPER; PASS ALL COLORED PAPER", etc.

The transmitter 12 can be described as having an array of red lights 58, an array of green lights 60, and an array of blue lights 62, each array being spaced across the width 21 of the conveyor belt 20.

Figures 12, 13, 14:
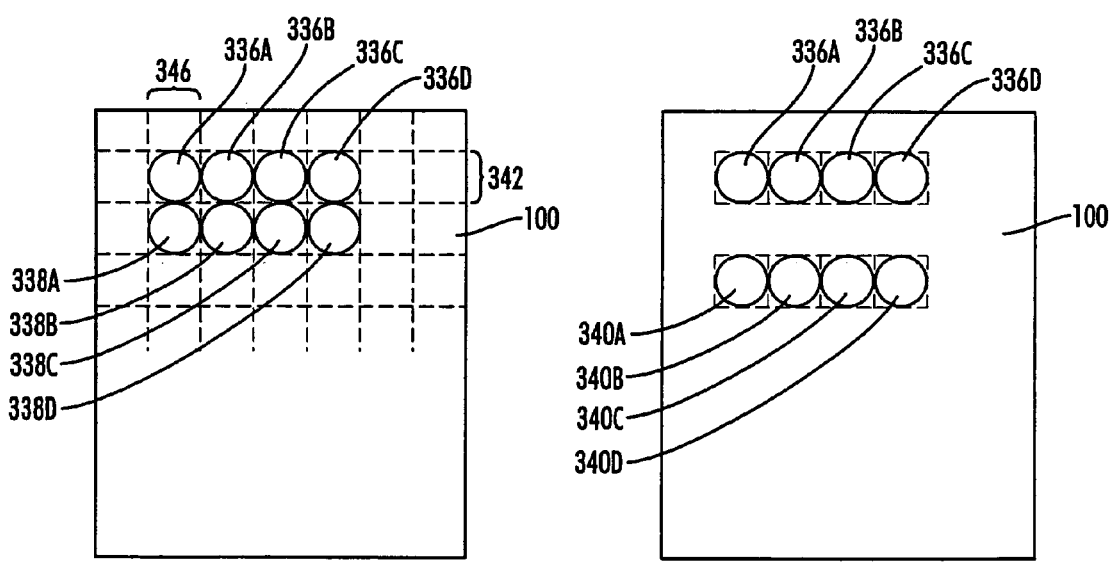
FIG. 12 illustrates a sort select screen.
FIG. 13 is a schematic illustration of a piece of paper showing adjacent portions or pixels of the paper which are observed by the receiver and sensors.
FIG. 14 is a view similar to FIG. 13 showing adjacent rows of pixels at a higher paper speed.

The receiver 14 can be described as including an array of sensors 64 spaced across the width 21 of the conveyor, each sensor 64 receiving light reflected from an area such as area 336 seen in FIG. 13 and defining one pixel 336 of a sheet of paper 100.

To illustrate the concept of pixels and adjacent areas on the paper 100, reference is made to FIG. 13. There an arbitrary piece of paper 100 is represented. Assuming for this example that each sensor 64 of receiver 14 observes a circular area or pixel 336 of diameter of ¾", and assuming the sensors 64 are spaced a distance of ¾" apart across the width 21 of conveyor belt 12, then the observed areas on paper 100 would correspond to observed areas such as 336A, 336B, 336C and 336D shown in FIG. 13. Any two of these pixels, such as 336A and 336B can be considered adjacent pixels. Then, depending upon the speed at which the control system 308 actuates the transmitter 12 and receiver 14, and depending upon the speed at which the conveyor belt 20 is moving the paper 100, the row of pixels 336 will be followed by a second row, which may directly abut the first row, such as second row of pixels 338A, 338B, 338C and 338D shown in FIG. 13. Or if the speed of the paper 100 is faster, the first row 336 may be followed by a spaced second row 340A, 340B, 340C and 340D as shown in FIG. 14. In either event, pixels such as 336A and 338A may be referred to as adjacent pixels, and in FIG. 14, pixels such as 336A and 340A may be referred to as adjacent pixels.

SUMMARY OF THE METHODS

The methods of the present invention can be generally summarized as follows. The paper 100 is conveyed on conveyor belt 20 through the inspection zone 306. At least three characteristics of the paper are analyzed as the paper passes through the inspection zone 306. Those three characteristics are the color of the paper, whether the paper is glossy, and whether the paper displays printed material. Then the paper is sorted based upon at least one of the characteristics analyzed in the analysis step.

The method may include a step of providing a logic map specifying values of parameters corresponding to the three characteristics for a plurality of categories of paper. The logic map could, for example, include information like that set forth in Table I, which information, of course, would be in digital form. The analysis step of the method includes a step of determining the parameters for paper of unknown category passing through the inspection zone 306, and comparing the parameters for the paper of unknown category to the values in the logic map and thereby determining the category of paper passing through the inspection zone 306. This determination can be performed, for example, by the method outlined and described with reference to FIG. 7.

The method may include a step of selecting a category of paper to be sorted from the other paper being conveyed through the inspection zone. This selection step may be executed by use of the sort select screen shown in FIG. 12.

The analysis step may include a step of measuring an intensity of light reflected from the paper and originating from first and second light sources of different colored light. This measuring step may be conducted in accordance with processes 201 and 211.

The parameters of the logic map may include a log slope of the intensities of the reflected light from the first and second sources as described in process 201 of FIG. 7.

The parameters of the logic map further include a color derivative representative of a difference in color of adjacent portions of the paper in the inspection zone as described with regard to process 223 in FIG. 7.

The parameters of the logic map may include a combined intensity of the reflected light from the first and second sources, as described in process 211 of FIG. 7.

The parameters of the logic map may include an intensity derivative representative of a difference in the presence of printed matter on adjacent portions of the paper in the inspection zone as described with reference to process 215 in FIG. 7.

The analysis step may also include the measuring of an intensity of reflected light reflected from the paper 100 and originating from first and second light sources 12 and 152 of the same color light, preferably infrared light. The first and second light sources 12 and 152 are differently oriented so that the measured reflected light from the first source 12 is diffuse reflected light and the measured reflected light from the second source 152 is directly reflected light. The parameters of the logic map may include a comparison of the diffuse reflected light from the first source 12 with the direct reflected light from the second source 152, which comparison is a representation of whether the paper is glossy or not. If the paper is not glossy, then the intensity of diffuse reflected light originating from first source 12 will be approximately equal to the intensity of directly reflected light originating from second source 152. If, however, the paper is glossy, it will be much more directly reflected light from second source 152.

The methods further include a high speed method of sorting paper. First, the paper is conveyed through the inspection zone 306 at a speed of at least 1,000 feet per minute, and more preferably at least 1,500 feet per minute. At least one characteristic of the paper is analyzed as the paper passes through the inspection zone. The at least one characteristic is selected from the group consisting of color, glossiness and the presence of printed matter. Then the paper is sorted downstream of the inspection zone based upon the analysis.

When the basis of analysis is to be the color of the paper, the paper will be exposed in the inspection zone to a plurality of sources of visible light of different wavelengths. The analysis step is then based upon a comparison of the paper's reflectivity of the different wavelengths of visible light. The plurality of separate beams of visible light preferably include red light, blue light and green light and that those lights are preferably provided by red, green and blue light emitting diodes.

When the characteristic to be analyzed is glossiness, the method includes steps of collecting diffuse reflected light reflected off the paper from a first light source, and collecting directly reflected light which may also be referred to as dielectric reflected light, reflected off the paper from a second light source 152. Then the analysis step includes analyzing the glossiness of the paper based upon a comparison of the diffuse reflected light to the dielectric reflected light.

As used herein the two different concepts of a diffuse reflected light beam and a directly reflected light beam are defined as follows. A light beam from source 152 which strikes a surface such as paper 100 at an angle such as 356 illustrated in FIG. 5, and then is reflected directly off of the surface of the paper at an opposite angle such as 358 along path 156 is referred to as directly reflected light or the dielectric reflection. On the other hand, light which is transmitted onto the paper such as along path 28 from mirror 16 illustrated in FIG. 5, and which then bounces off the irregular surface texture of the paper to scatter in all directions, a small portion of which would travel back along the path 30, is referred to as diffuse reflected light. The typical angle 358 to the vertical at which the receiver 14 observes the inspection zone 306 is approximately 30°. This prevents any gloss on the surface of the paper 100 or the belt 20 itself from causing a false reading of high reflectivity. For example, black plastic might read as white due to the high reflection caused by the shiny surface if the receiver 14 was oriented perpendicular to the belt 20. The reflected light characteristics that are sensed to determine color of the paper are those reflections which are due to the diffuse reflection from the surface texture of the paper 100, and not the dielectric or direct reflection from the boundary surface which is due to gloss of the paper.

When the characteristic to be analyzed is the presence of printed matter, the method may include a step of comparing the intensities of the light reflected from adjacent pixels such as 336A and 336B or such as 336A and 338A or such as 336A and 340A, to identify paper with varying reflectance from adjacent pixels resulting from the presence of printed matter on the paper.

Similarly, the paper may be analyzed for the presence of a varying color between adjacent pixels to identify the presence of printed matter.

When the method is based upon an analysis of the color of the paper, a technique may be utilized to correct for dynamic aberration of the sensed color of the paper moving within the inspection zone. This method includes sequentially exposing the paper in the inspection zone 306 to the plurality of separate beams of visible light of different wavelengths in a first sequence and then in a second sequence which is a reverse of the first sequence, so that two reflected light signals are generated for each wavelength of light. Then the analysis step includes combining the analysis of the two reflected light signals for each wavelength of light to correct for dynamic aberration. Preferably, the combined analysis includes averaging the two reflected light signals. These sequence of lights may also include one or more infrared light sources.

The following example is provided to illustrate the relative time duration of the various activities which occur during the color analysis process.

EXAMPLE 1

Figure 15:
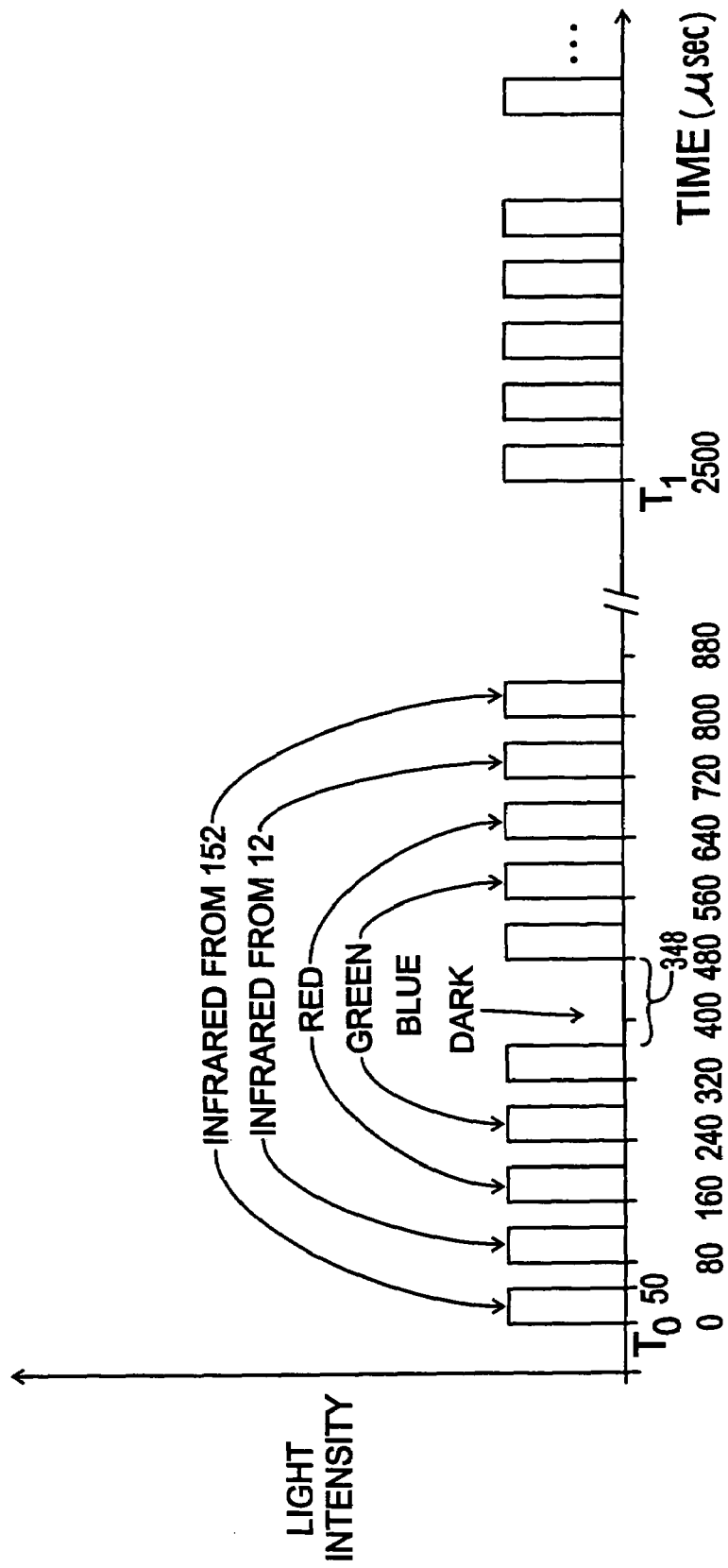
FIG. 15 is a graphic illustration of the sequential series of pulses associated with a single pixel or area on the paper being examined.

The paper 100 is moving through the inspection zone 306 at a speed of 1,500 feet per minute which is equal to 300 inches per second. The size of each pixel 336 is determined by the observation area of one of the sensors 64 which is a circular area having a diameter from about ¾" to 1". Thus each pixel can be considered to have a length 342 and a width 346, each of about ¾". If the cycle time between repetitions of the sequence of interrogating lights is set at 2,500 microseconds, the process will repeat 400 times per second, and thus, adjacent rows of pixels 336 and 338 will repeat every ¾" and will abut as shown in FIG. 13. FIG. 15 is a schematic illustration of the timing of these various pulses as they would appear if displayed on an oscilloscope screen. Each pulse of one of the light emitting diodes last for a duration of 50 microseconds. The LED flashes begin 80 microseconds apart. The time interval between the center line of adjacent pixels 336A and 338A is 2,500 microseconds. The 2,500 microsecond time that it takes a given pixel length 342 to pass across a point in the inspection zone 36 is divided as follows. There are eleven periods of LED flashing to provide the first sequence of infrared from gloss source 152, infrared from first source 12, red, green, blue, then dark, then blue, then green, then red, then infrared from source 12, and then infrared from source 152. Each pulse has a duration of 50 microseconds and there is an interval of 80 microseconds between the beginning of adjacent pulses, thus resulting in a total of 880 microseconds during which the various lights are flashing. This leaves 1,620 microseconds during which no light from either of the sources is illuminating the inspection zone. With reference to FIG. 13, it will be appreciated that because the paper is moving, the receiver 14 will actually examine light received from an area slightly longer in length than the ¾41 length 342 which is being examined at any given point in time, because of the fact that the paper moves a short distance during the 880 microsecond duration of the series of eleven flashes. The actual ¾" length area being analyzed by the sequential series of flashes is best conceptualized as being the ¾" long area which the receiver 14 examines during the "dark" interval 348 in between the first series of flashes and the second reverse order series of flashes. Because the nested pairs of flashes of each color on either side of the dark interval 348 are averaged, they represent the reflected intensity of each of those colors that would have occurred at the spot being observed during the dark interval 348 if the paper had in fact not been moving. As can be seen in the example just described, the first and second series of sequential flashes are performed during an interrogation time interval of 880 microseceends which is less than the 2,500 microsecond time required for a pixel of an object equal in size to the inspection zone to move through the inspection zone.

Of course as previously noted the belt speed can be increased so that adjacent rows of pixels are not physically abutting each other, as for example, in the alternative example illustrated in FIG. 14.

When using the normalization system illustrated in FIGS. 1 and 2, the method may be described as including steps of conveying paper 100 through the inspection zone 306, then transmitting light from an array of light sources 12 onto a mirror 16 which reflects the light onto the inspection zone 306. The light in the inspection zone is reflected off the paper 100 back to the mirror 16 and then back to an array of sensors in receiver 14, which array of sensors generate signals corresponding to characteristics of the paper 100 in the inspection zone 306. Periodically, it may be necessary to normalize or calibrate the various sensors of the array of sensors contained in receiver 14, and this is accomplished by rotating or moving the mirror 16 to the normalization position illustrated in FIG. 2 where the light from the array of light source 12 is reflected from the mirror 16 onto the reference surface 24. During that time, outputs from the array of sensors in receiver 14 may be normalized with reference to the light reflected from the reference surface 24. During this process the light being directed to the reference surface 24 preferably travels through a reference wear cover 22 which has properties of light transmission substantially the same as those of wear cover 18, thus simulating the light which should be received by the receiver 14 from a white object on conveyor belt 20.

These normalization procedures may be executed automatically on a periodic basis. They may also be executed automatically upon start up of the apparatus. They may also be executed intermittently based upon individual direction from the human operator.

When the receiver 14 is normalized or calibrated, each of the photo diodes of the receiver 14 will have its corresponding output adjusted so that each photo diode sensor 68 has the same output for an identical paper pixel 336 located thereunder. Thus, once the receiver array 14 has been normalized, if a large sheet of white paper or any other uniform color paper passes through the inspection zone 306 covering the entire inspection zone, each sensor should have an identical output. When the receiver is directed to the reference surface, the microprocessor adjusts all signals to read 100%. Thus, when the receiver is redirected to the belt 20 in normal operating position, the receiver 14 has been calibrated so that a piece of white Teflon passing along the belt 20 should also result in a 100% reflection for all colors.

It will be appreciated that it would not be practical to normalize the receivers with reference to the black conveyor belt 20 for several reasons. First, the belt is black which normally has a zero reflectance, and normalization at zero output is not effected. Furthermore, the belt becomes dirty with use.

This normalization technique is important because the actual signals that will be measured when objects pass through the inspection zone 306 are based upon changes in output, and it is important to have a normalized base signal to which that change can be compared. As noted, this normalization procedure could take place periodically (e.g., once per hour) during the operation of the apparatus 10. A normalization cycle involving rotation of the mirror 16 and then return to the operating position would typically not take more than 3 to 5 seconds. Thus, it is practical to perform the normalization as the apparatus 10 is operating, as only a very small amount of paper will pass through the inspection zone 306 and not be properly sorted during the normalization cycle.

Thus, it is seen that the apparatus and methods of the present invention readily achieve the ends and advantages mentioned as well as those inherent therein. While certain preferred embodiments of the invention have been illustrated and described for purposes of the present disclosure, numerous changes may be made by those skilled in the art, which changes are encompassed within the scope and spirit of the present invention as defined by the appended claims.

What is claimed is:

1. A method of sorting paper, comprising:
   (a) moving the paper through an inspection zone;
   (b) transmitting a first light beam from a first source onto the paper;
   (c) receiving a diffuse reflected first light beam, reflected from the paper as a result of the first light beam;
   (d) transmitting a second light beam from a second source onto the paper;
   (e) receiving a directly reflected second light beam, reflected from the paper as a result of the second light beam;
   (f) analyzing a glossiness of the paper based upon a comparison of the diffuse reflected first light beam to the directly reflected second light beam; and
   (g) sorting the paper based upon the glossiness of the paper.

2. The method of claim 1, wherein:
   the first and second light beams of steps (b) and (d) are light beams of the same wavelengths.

3. The method of claim 2, wherein:
   the first and second light beams are both infrared light.

4. The method of claim 2, wherein:
   the second source is a diffuse source so that glossiness of crumpled paper can be detected.

5. The method of claim 1, wherein:
   the first and second light beams in steps (b) and (d) are transmitted at opposite angles on opposite sides of a plane normal to a direction in which the paper is moving.

6. The method of claim 1, wherein:
   steps (b) and (c) occur prior to steps (d) and (e).

7. The method of claim 1, wherein:
   steps (d) and (e) occur prior to steps (b) and (c).

8. The method of claim 1, wherein:
   step (f) includes comparing an intensity of the diffuse reflected first light beam to an intensity of the direct reflected second light beam; and determining that the paper is not glossy if the intensities are substantially equal.

9. An apparatus for sorting paper, based on glossiness comprising:
   a conveyor for conveying paper through an inspection zone;
   first and second light sources for transmitting light onto the inspection zone;
   a sensor for receiving light reflected from the inspection zone;
   the first light source is oriented so that the sensor receives diffuse reflected light from the first light source; and
   the second light source is oriented so that the sensor receives directly reflected light from the second light source.

10. The apparatus of claim 9, wherein:
    the first and second light sources transmit the same color of light.

11. The apparatus of claim 10, wherein the light is infrared.

12. The apparatus of claim 10, wherein the first and second light sources are light emitting diodes.

13. The apparatus of claim 9, wherein:
    the first and second light sources are located on opposite sides of an imaginary plane normal to the direction of conveyance of the paper and passing through the inspection zone.

14. The apparatus of claim 13, further comprising:
    the first light source being oriented in a direction parallel to the direction of conveyance of the paper;
    a mirror oriented to reflect light from the first light source onto the inspection zone; and
    the second light source is oriented to direct light from the second light source directly onto the inspection zone.

15. The apparatus of claim 14, wherein:
    the second light source is a wide diffuse light source to accommodate detection of glossy paper which is not lying exactly flat upon the conveyor.

* * * * *